United States Patent [19]

Maier et al.

[11] 4,173,647
[45] Nov. 6, 1979

[54] 4-SPECTINOMYCYLAMINE AND SALTS THEREOF

[75] Inventors: Roland Maier; Eberhard Woitun, both of Biberach, an der Riss; Wolfgang Reuter, Laupertshausen; Bernd Wetzel; Hanns Goeth, both of Biberach, an der Riss; Uwe Lechner, Ummendorf, all of Fed. Rep. of Germany

[73] Assignee: Boehringer Ingelheim GmbH, Ingelheim am Rhein, Fed. Rep. of Germany

[21] Appl. No.: 965,869

[22] Filed: Dec. 4, 1978

[30] Foreign Application Priority Data

Dec. 21, 1977 [DE] Fed. Rep. of Germany ....... 2756914

[51] Int. Cl.² .................. A61K 31/35; C07D 311/02; C07D 319/08
[52] U.S. Cl. ................................ 424/283; 260/340.3; 546/197; 546/187
[58] Field of Search ...................... 260/340.3; 424/283

[56] References Cited

U.S. PATENT DOCUMENTS 3,147,277  9/1964  Hoeksema .......................... 260/340.3
3,165,533  1/1965  Hoeksema et al. ................ 260/340.3

Primary Examiner—Ethel G. Love
Attorney, Agent, or Firm—Hammond & Littell

[57] ABSTRACT

The compound of the formula

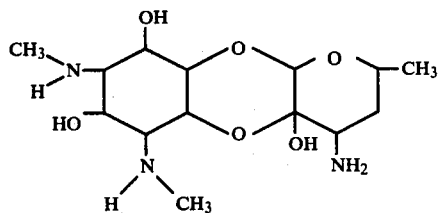

and non-toxic, pharmacologically acceptable acid addition salts thereof. The compound as well as its salts are useful as antimicrobials.

4 Claims, No Drawings

4-SPECTINOMYCYLAMINE AND SALTS THEREOF

This invention relates to the novel compound 4-spectinomycylamine and non-toxic, pharmacologically acceptable acid addition salts thereof, as well as to methods of preparing these compounds, pharmaceutical compositions containing them as active ingredients, and methods of using them as antimicrobials.

More particularly, the present invention relates to the compound of the formula

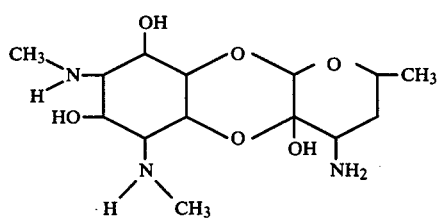

which can be named 4-spectinomycylamine or also decahydro-4a,7,9-trihydroxy-4-amino-2-methyl-6,8-bis(methylamino)-pyrano[2,3-b][1,4]benzodioxin, and non-toxic, pharmacologically acceptable acid addition salts thereof.

The compound of the formula I above may be prepared by the following methods:

Method A

By reducing a spectinomycin derivative of the formula

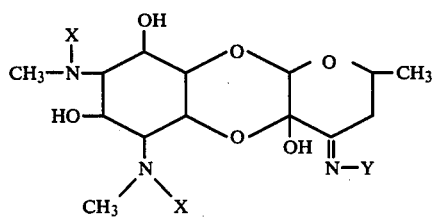

wherein

X represents a hydrogen atom; an organic group which is known from peptide chemistry and is easily removable by reduction, such as the benzyloxycarbonyl group, the 4-bromine or 4-nitro or 4-chloro-benzyloxycarbonyl group, the 4-methoxy- or 3,4-dimethoxy- or 3,4-methylenedihydroxy- or 3,4,5-trimethoxy- or 4-decyloxy- or 4-acetoxy- or 4-ethoxy-carbonyloxybenzyloxycarbonyl group; a phenyl or biphenylalkoxycarbonyl group which may be substituted by one to three methyl or methoxy groups and the alkylene moiety of which may be straight or branched contains 2 to 4 carbon atoms, as for example the α,α-dimethyl-3,5-dimethoxy-benzyloxy-carbonyl or 2-[biphenylyl-(4)]propyl-(2)-oxycarbonyl group, which may be substituted optionally by a nitro, methoxy or methyl group; a dialkylaminooxycarbonyl group such as the dimethylaminooxy carbonyl group or the piperidinooxy carbonyl group; or also a benzyl or trityl group; and Y represents the hydroxyl group, an alkoxy group with 1 to 10 carbon atoms, the phenalkoxy group with altogether 7 to 12 carbon atoms, or a group of the formula

wherein $R_1$ and $R_2$ represent hydrogen atoms, alkyl groups with 1 to 6 carbon atoms, phenalkyl groups with altogether 7 to 10 carbon atoms or the phenyl group; or $R_1$ can also be an aliphatic acyl group with 1 to 10 carbon atoms or the benzoyl group, and $R_2$ has the meanings mentioned above; or Y is a group of the formula

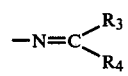

wherein $R_3$ and $R_4$ represent hydrogen atoms, alkyl groups with 1 to 6 carbon atoms, phenalkyl groups with 7 to 10 carbon atoms or the phenyl group, or $R_3$ and $R_4$, together with the carbon atom to which they are attached, can also form a 5- to 8-membered carbocyclic ring.

Especially suitable for the reduction is catalytic hydrogenation in the presence of metal catalysts, such as for example finely divided platinum, palladium or platinum dioxide. The hydrogenation is carried out in water, in organic solvents such as alcohols, carboxylic acids, dioxane, tetrahydrofuran or in mixtures of these solvents, at temperatures between 0° and 100° C., preferably at temperatures between 20° and 50° C. and at pressures between 1 and 100 atmospheres.

Of advantage in this method is the addition of inorganic or organic acids such as hydrogen chloride, hydrogen bromide, trifluoroacetic acid, methanesulfonic acid or trifluoromethane-sulfonic acid.

Method B

By removal of the radicals X' from a 4-spectinomycylamine derivative of the formula

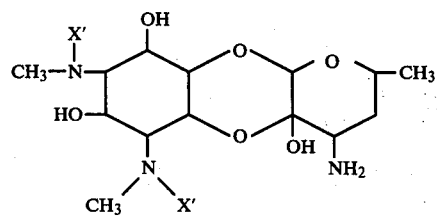

wherein

X' represents an organic group which is known from peptide chemistry and is easily removable by treatment with acids or bases or by reduction; such a group may be the benzyloxycarbonyl group, the 4-bromo or 4-nitro or 4-chloro-benzyloxycarbonyl group, the 4-methoxy- or 3,4-dimethoxy- or 3,4-methylene-dihydroxy- or 3,4,5-trimethoxy- or 4-decyloxy- or 4-acetoxy or 4-ethoxycarbonyloxybenzyloxycarbonyl group; a saturated or unsaturated alkoxycarbonyl group with 1 to 12 carbon atoms, which may be substituted optionally by a furyl-(2)-group, a p-tolylsulfonyl group, one or more halogen atoms, an alkoxy or alkoxy-alkoxy group with 1 to 3 carbon atoms in the alkyl moity and 1 to 3 carbon atoms in the alkylene moiety, for example the furyl-(2)-methoxycarbonyl, allyloxycarbonyl, 2-(p-tolylsulfonyl)-ethoxycarbonyl, 2-bromo-ethoxycarbonyl, 2,2,2-trichloroethoxycarbonyl, 2-(2-methoxy-ethoxy)-ethoxycarbonyl, 3-methyl-pentyl-(3)-oxycarbonyl, but particularly the tert. butyloxycarbonyl group; a cycloalkyloxycarbonyl group with 5 to 12 carbon atoms, such as the cyclopentyloxycarbonyl or cyclohexyloxycarbonyl group, which may both be substituted by a methyl, ethyl or tert. butyl group; the isobornyloxycarbonyl or the adamantyl-(1)-oxycarbonyl group; a phenyl or biphenyl-alkoxy carbonyl group, which may be substituted by one to three methyl or methoxy groups in the phenyl moiety, and the alkylene group thereof, which may be straight or branched, contains 2 to 4 carbon atoms, such as for example the α,α-dimethyl-3,5-dimethoxy-benzyloxycarbonyl or 2-[biphenylyl-(4)]propyl-(2)-oxycarbonyl group; the diphenyl-methoxycarbonyl group; a phenyloxycarbonyl group, which may be substituted optionally by a nitro, methoxy or methyl group; a dialkylaminooxycarbonyl group such as the dimethylaminooxycarbonyl group or the piperidinooxycarbonyl group; an alkylthiocarbonyl group with 1 to 4 carbon atoms in the alkyl radical; the benzylthiocarbonyl group; the formyl group or another aliphatic acyl group with 1 to 10 carbon atoms, which may be substituted optionally by 1 to 3 halogen atoms, hydroxyl groups, acyl radicals or by a nitro group, such as the trifluoroacetyl, acetoacetyl, 2-nitro-phenoxyacetyl, monochloroacetyl, 3-chloro-butyroyl, 3-hydroxyisocaproyl group; furthermore, X' can represent a benzoyl, 2-nitrobenzoyl, 4-toluene sulfonyl, benzylsulfonyl or p-methoxybenzene sulfonyl group or also a benzyl or trityl group.

The removal of the radical X' is carried out, for example, by means of catalytic hydrogenation in aqueous-organic or only organic solvents, such as alcohols, acetic acid or dimethylformamide, in the presence of precious metal catalysts such as palladium black, palladium-on-coal or palladium-on-barium sulfate, platinum-on-coal; or by reductive removal with sodium in liquid ammonia; or by an acid cleavage with a hydrohalic acid, such as hydrogen chloride, hydrogen bromide, trifluoroacetic acid or an organic sulfonic acid, in solvents such as glacial acetic acid, chloroform, water or ethanol. Alkoxycarbonyl groups can be removed by the action of sodium hydroxide in water-ethanol-mixtures, or by the action of sodium ethanolate in ethanol. The optionally substituted phenyloxycarbonyl groups or benzyloxycarbonyl as well as the dialkylaminooxycarbonyl groups can be removed by catalytic hydrogenation. Acyl radicals can be especially well removed by the action of methanolic hydrochloric acid or aqueous alkalis. The 2,2,2-trichloro-ethoxycarbonyl group is advantageously removed by the action of zinc powder in acetic acid or by the action of zinc dust in methanol. However, the benzyl group is preferably removed by catalytic hydrogenation with palladium, the trityl group by acid hydrolysis with acetic acid. Most of the groups X' can, however, be removed for example with hydrogen bromide in glacial acetic acid at temperatures between 20° and 50° C.

If desired, the 4-spectinomycylamine of formula I can subsequently be converted into a non-toxic, pharmacologically acceptable acid addition salt thereof with an inorganic or organic acid according to known methods. Suitable such acids are, for example: Hydrochloric acid, hydrobromic acid, sulfuric acid, phosphoric acid, maleic acid, citric acid, tartaric acid or fumaric acid.

A starting spectinomycin derivative of the formula II can be prepared from a spectinomycin derivative of the formula

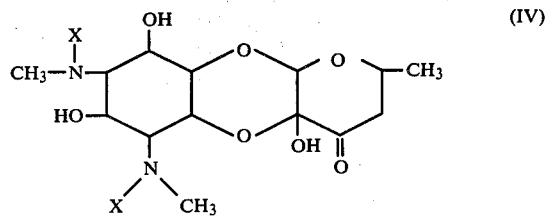

wherein X is as defined above, by reaction with a compound of the formula

$$NH_2-Y \qquad (V)$$

wherein Y also is as defined above. The reaction is carried out in water or in an organic solvent, for example in alcohols such as ethanol or isopropanol, in carboxylic acids such as glacial acetic acid, in esters, or in ethers such as dioxane, or in mixtures of such solvents, at temperatures between 0° and 100° C., preferably at temperatures between 0° and 50° C.

The starting 4-spectinomycylamine derivatives of the formula III can also be obtained from compounds of the formula IV, namely by reaction with ammonium salts in the presence of alkali metal cyanoborohydrides. The reaction is carried out in water or in organic solvents, preferably in alcohols or in mixtures of them at temperatures between 0° and 100° C., preferably at temperatures between 0° and 50° C. Suitable ammonium salts are, for example, the salts of ammonia with hydrohalic acids, sulfuric acid, phosphoric acid or nitric acid; a suitable alkali metal cyanoborohydride is preferably sodium cyanoborohydride.

The starting compounds of the formula III, wherein X' possesses the above mentioned meanings except the meaning of a group which is easily removable by reduction (the groups removable by reduction are those which are indicated above for X in formula II), can be obtained by reducing compounds of the formula II, having instead of X a radical X', for example by catalytic hydrogenation.

In the preparation of 4-spectinomycylamine of the formula I two isomeric compounds occur, namely the 4-R-form with an axial amino group and the 4-S-form with an equatorial amino group. The 4-R-form is designated as 4-spectinomycylamine I and has an $R_f$-value of 0.5, while the 4-S-form, designated as 4-spectinomycylamine II, has an $R_f$-value of 0.4 [adsorbant: silica gel G; eluant: chloroform:methanol:conc. ammonia (40:40:20)].

Therefore, it is easy to separate the isomers from each other by means of chromatographic methods. It was possible to assign the $R_f$-values to the respective isomers because these isomers showed different chemical behavior, for example upon reaction with acetone or with methyl-2-cyano-3, 3-bis-(methyl)-mercaptoacrylate.

Both spectinomycylamine isomers possess useful antimicrobial properties; especially pronounced are the properties in the 4-R-form, that is in 4-spectinomycylamine I.

The following examples illustrate the present invention and will enable others skilled in the art to understand it more completely. It should be understood, however, that the invention is not limited solely to the particular examples given below.

I. Preparation of starting compounds

EXAMPLE A

Spectinomycin-benzyloxime 6 gm (0.012 mol) of spectinomycin dihydrochloride pentahydrate and 3 gm of o-benzylhydroxylamine were dissolved in 25 ml of water and 25 ml of methanol. The solution was stirred overnight, then evaporated, the residue was dissolved in a little absolute ethanol, and ether was added until turbidity set in. 5.0 gm (83% of theory) of a colorless powder were obtained. Decomposition point 175° C.

$R_f$: 0.8 (silica gel, chloroform/methanol/conc. ammonia = 20:20:3).

NMR-spectrum (solvent $CD_3OD$).

ppm: 1.3—(doublet, 3H ≙ 2—$CH_3$—), 2.8—(doublet, 6H ≙ —N—$CH_3$, 4.65—(singlet, 1H ≙ 10aH), 5.2—(singlet, 2H ≙ benzyl—$CH_2$), 7.4—(singlet, 5H ≙ phenyl).

The free compound was obtained by adding an ion exchanger [Dowex 2×8 ($\overline{OH}$-form)] to an aqueous-methanolic solution of the dihydrochloride until the pH-value remained at 10.4. Colorless crystals having a melting point of 86°–106° C. were obtained.

Analogously were obtained:

(a) 6,8-Bis-benzyloxycarbonyl-spectinomycin-oxime from 6,8-bis-benzyloxycarbonyl-spectinomycin and hydroxylamine $R_f$: 0.38 (silica gel, chloroform/methanol=9:1) $C_{30}H_{37}N_3O_{11}$ (615.6)

Calc.: C-58.52%; H-6.06%; N-6.82%; Found: C-58.00%; H-6.21%; N-6.65%.

The starting material, 6,8-bis-benzyloxycarbonyl-spectinomycin is known from the literature [J. Amer. Chem. Soc. 85, 2657 (1963)].

(b) 6,8-Bis-benzyloxycarbonyl-spectinomycin-methyloxime from 6,8-bis-benzyloxycarbonyl-spectinomycin and O-methyl-hydroxylamine, $R_f$: 0.40 (silica gel; chloroform/methanol=9:1).

(c) Spectinomycin-benzhydrazone dihydrochloride from spectinomycin dihydrochloride pentahydrate and benzoylhydrazine, Point of decomposition: 180° C.

$R_f$ = 0.35 (cellulose, butanol/methanol/water=90:25:20).

(d) Spectinomycin-acethydrazone dihydrochloride from spectinomycindihydrochloride pentahydrate and acetylhydrazine, Point of decomposition: 160°–180° C.

$R_f$: 0.29 (cellulose, butanol/methanol/water=90:40:20).

EXAMPLE B 6,8-Bis-$\beta,\beta,\beta$-trichloroethoxycarbonyl-spectinomycin-benzyloxime 6 gm (0.008 mol) of 6,8-bis-$\beta,\beta,\beta$-trichloroethoxycarbonylspectinomycin and 1.5 gm (0.01 mol) of O-benzyl-hydroxylamine hydrochloride were dissolved in 40 ml of dioxane and 40 ml of water. solution was solutionwas adjusted to a pH-value of 3 to 4 by addition of 4 N sodium hydroxide. After stirring for 18 hours at room temperature, the mixture was stirred into 150 ml of water and extracted with ethyl acetate. The organic phase was dried and evaporated. 6 gm (93% of theory) of a colorless product were obtained.

$R_f$: 0.30 (silica gel, chloroform/methanol-9:1) NMR (solvent: Deuterochloroform)

ppm: 1.35 doublet 2H (2—$CH_3$), 3.15 doublet 6H (—N—$CH_3$), 4.7 singlet 1H (10aH), 4.8 broad singlet 2H (—$CH_2$—$CCl_3$), 5.2 singlet 2H (benzyl—$CH_2$), 7.4 singlet 5H (phenyl).

The starting material, 6,8-bis-$\beta,\beta,\beta$-trichloroethoxycarbonyl-spectinomycin can be prepared from spectinomycin and $\beta,\beta,\beta$-trichloroethyl-chloroformate according to the method described in J. Antibiotics XXVIII, p.140 (1975) for 6,8-bis-benzyloxycarbonyl-4-dihydro-spectinomycin.

$R_f$: 0.26 (silica gel, chloroform/methanol=11.1)

Analogously the following compounds were obtained:

(a) 6,8-Bis-p-methoxy-benzenesulfonyl-spectinomycin-oxime from 6,8-bis-p-methoxy-benzenesulfonyl-spectinomycin and hydroxylamine.

$R_f$: 0.32 (silica gel, chloroform/methanol=11:1).

The starting material, 6,8-bis-p-methoxybenzenesulfonyl-spectinomycin was obtained from p-methoxybenzenesulfochloride and spectinomycin as indicated above.

$R_f$: 0.40 (silica gel, chloroform/methanol=9:1).

(b) 6,8-Bis-isobornyloxycarbonyl-spectinomycin-benzyloxime from 6,8-bis-isobornyloxycarbonyl-spectinomycin and O-benzyl-hydroxylamine.

$R_f$: 0.55 (silica gel, chloroform/methanol=10:1), M.p.: 120° C. (decomp.).

The starting material was prepared from spectinomycin and isobornyloxycarbonyl chloride as indicated above;

$R_f$: 0.42 (silica gel, chloroform/methanol=10:1).

EXAMPLE C 6,8-Bis-benzyloxycarbonyl-spectinomycylamine 1.85 gm (0.003 mol) of 6,8-bis-benzyloxycarbonyl-spectinomycin and 2.4 gm of ammonium nitrate were dissolved in 15 ml of absolute methanol, and the solution was stirred for 15 minutes at 40° C. Subsequently, 0.131 gm of sodium cyanoborohydride was added in portions over a period of 3 minutes at 20° C. After stirring for 30 minutes at room temperature the mixture was suction-filtered, the filtrate was stirred into 70 ml of a saturated aqueous solution of sodium chloride, extracted with ethyl acetate, and the extract was dried and evaporated. The residue was triturated with ether and suction-filtered. This residue (1.2 gm) was chromatographed on silica gel (chloroform/methanol=5.1). 0.6 gm of a colorless powder were obtained. Range of decomposition 110°–130° C.

$C_{30}H_{39}N_3O_{10}$ (601.66)

Calc.: C-58,89%; H-6.53%; N-6.57%; Found: C-59.10%; H-6.99%; N-6.76%.

Mass spectrum of the silylated product:

$M^+$: 817=601+3X72 (3 silyl radicals), 745=601+2X72 (2 silyl radicals).

$R_f$: 0.47 (silica gel, chloroform/methanol=5:1)

Analogously were prepared:

(a) 6,8-Bis-p-methoxy-benzenesulfonyl-spectinomycylamine from 6,8-bis-p-methoxy-benzenesulfonyl-spectinomycin, ammonium nitrate and sodium cyanoborohydride, R$_f$: 0.55 (silica gel, chloroform/methanol = 9:1)

(b) 6,8-Bis-$\beta,\beta,\beta$-trichloroethoxycarbonyl-spectinomycylamine from 6,8-bis-$\beta,\beta,\beta$-trichloroethoxycarbonyl-spectinomycin, ammonium nitrate and sodium cyanoborohydride.

R$_f$: 0.41 (silica gel, chloroform/methanol = 9:2)
Mass spectrum of the silylated compound:
M$^+$: 969 = 681 + 4X72 (4 silyl radicals)
Calculated weight of molecule: 684.18.

(c) 6,8-Bis-isobornyloxy-carbonyl-spectinomycylamine from 6,8-bis-isobornyloxycarbonyl-spectinomycin, ammonium nitrate and sodium cyanoborohydride,
Mass spectrum of the silylated substance:
M$^+$: 909 = 693 + 3X72 (3 silyl radicals), 837 = 693 + 2X72 (2 silyl radicals), 693 = calculated molecular weight.
M.p.: 160° C. (decomp.)

(d) 6,8-Bis-4-methoxy-benzyloxycarbonyl-spectinomycylamine from 6,8-bis-4-methoxy-benzyloxycarbonyl-spectinomycin, ammonium nitrate and sodium cyanoborohydride.

R$_f$: 0.29 (silica gel, chloroform/methanol 5:1)
Mass spectrum of the silylated compound:
M$^+$: 877 = 661 + 3X72 (3 silyl radicals).
Calculated molecular weight: 661.6.

EXAMPLE D 6,8-Bis-isobornyloxycarbonyl-spectinomycylamine 7.98 gm (0.01 mol) of 6,8-bis-isobornyloxycarbonyl-spectinomycin-benzyloxime were dissolved in 150 ml of 3% ethanolic hydrochloric acid and reduced with hydrogen at 25° C. in the presence of 8 gm of platinum oxide. (hydrogen pressure: 5 atmospheres; reaction time 62 hours).

After completion of the reduction the catalyst was suction-filtered off, and the ethanol was distilled off in vacuo. The remaining solid residue was dissolved in water. The pH-value of the solution was adjusted to 3.5, and the side-products were separated by extraction with ether. Subsequently, the pH-value of the solution was increased to 7.0, and the solution was again extracted with ether. After drying with sodium sulfate and evaporating the ether, the desired product was obtained in the form of a white powder.

Yield: 4.1 gm (59% of theory),
M.p.: 160° C. (decomp.).
C$_{36}$H$_{59}$N$_3$O$_{10}$ (693.97)
Calculated: C-49.41%; H-6.12%; N-8.23%; Found: C-49.29%; H-6.25%; N-8.37%.

The hydrochloride was obtained by treating an ethanolic solution of the free base with ethereal hydrochloric acid. M.p.: 182°–185° C.

Analogously were obtained:

(a) 6,8-Bis-$\beta,\beta,\beta$-trichloroethoxycarbonyl-spectinomycylamine from 6,8-bis-$\beta,\beta,\beta$-trichloroethoxycarbonyl-spectinomycinbenzyloxime and platinum dioxide, R$_f$: 0.41 (silica gel, chloroform/methanol 9:2)
Mass spectrum of the silylated compound:
M$^+$: 969 = 681 + 4X72 (4 silyl radicals), 897 = 681 + 3X72 (3 silyl radicals), 825 = 681 + 2X72 (2 silyl radicals).
calculated molecular weight: 684.18.

(b) 6,8-Bis-p-methoxybenzenesulfonyl-spectinomycylamine from 6,8-bis-p-methoxybenzenesulfonyl-spectinomycinoxime and platinum dioxide, R$_f$: 0.55 (silica gel, chloroform/methanol = 9:1)

Preparation of end products:

EXAMPLE 1

4-R-Spectinomycylamine trihydrochloride 500 mgm of 6,8-bis-benzyloxycarbonyl-spectinomycylamine (R-form) were hydrogenated in a mixture of 25 ml of 3.4% ethanolic hydrochloric acid and 500 mgm of 20% palladium-on-charcoal for two hours at room temperature in a shaking bulb. The catalyst was filtered off, the filtrate was evaporated to 5 ml, and 100 ml of ether were added to the residue. 230 mgm (65% of theory) of a colorless powder were obtained.

M.p.: 189°–194° C.
R$_f$: 0.5 (silica gel, chloroform/methanol/conc. ammonia = 40:40:15)
Mass spectrum of the silylated compound:
M$^+$: 693 = 333 + 5X72 (5 silyl radicals), 621 = 333 + 4X72 (4 silyl radicals), 549 = 333 + 3X72 (3 silyl radicals), 477 = 333 + 2X72 (2 silyl radicals).
Calculated molecular weight of the free base: 333.

EXAMPLE 2

4-R-Spectinomycylamine trihydrochloride 5 gm of spectinomycin-benzyloxime dihydrochloride were hydrogenated in 500 ml of 3.4% ethanolic hydrochloric acid in the presence of 6.25 gm of platinum dioxide at room temperature for 30 hours (pressure 15 atmospheres). The catalyst was then filtered off, and the filtrate was evaporated to 100 ml. The obtained crystals were filtered off.

Yield: 2.5 gm (59% of theory).
Mass spectrum of the silylated compound:
M$^+$: 621 = 333 + 4X72 (4 silyl radicals),
Calculated molecular weight of the free base: 333.

The free base was obtained by adjusting the aqueous solution of the hydrochloride to a pH-value of 10.9 with an ion exchanger (Dowex 2×8 OH-form), and evaporating the aqueous solution in a high vacuum.

M.p.: 114°–117° C. (decomp.).

EXAMPLE 3

4-S-Spectinomycylamine trihydrobromide 10 ml of a 20% solution of hydrogen bromide in glacial acetic acid were added to 1 gm (0.00145 mol) of 6,8-bis-isobornyloxycarbonyl-spectinomycylamine (S-form) at 20° C. After 2 minutes 100 ml of absolute ether were added to the reaction mixture. The precipitating crystals were centrifuged off, washed three times with absolute ether and dried. The desired compound was thus obtained in pure form.

Yield: 0.65 gm (78% of theory),
M.p.: 208°–212° C. (decomp.).
C$_{14}$H$_{27}$N$_3$O$_6$.3HBr (576.14).
Calc. C-29.18%; H-5.24%; N-7.29%; Br-41.60%; Found: C-29.64%; H-5.39%; N-7.01%; Br-41.35%.

EXAMPLE 4

4-R-Spectinomycylamine trihydrochloride

A solution of 6.84 gm (0.01 mol) of 6,8-bis-trichloroethoxycarbonyl-spectinomycylamine (R-form) in 200 ml of 70% methanol was refluxed after addition of 14 gm of zinc powder. The reaction mixture was then suction-filtered, and the filtrate was evaporated in vacuo. The residue was dissolved in a little methanol and purified column-chromatographically. (adsorbant: silica gel G;

eluant: chloroform/methanol/conc. aqueous ammonia=20:20:5).

The fractions containing the desired product were combined and carefully evaporated in vacuo.

The residue was dissolved in 0.1 N hydrochloric acid and freeze-dried. The desired substance was obtained as a white powder.

Yield: 2.1 gm (47% of theory)
M.p.: 189°–194° C. (decomp.)
$C_{14}H_{27}N_3O_6.3$ HCl (442.79)
Calc.: C-37.98%; H-6.83%; N-9.49%; Cl-24.02%,
Found: C-38.12%; H-6.99%; N-9.27%; Cl-23.62%.

EXAMPLE 5

4-R-Spectinomycylamine trihydrochloride 500 mgm of 6,8-bis-p-methoxybenzenesulfonyl-spectinomycylamine (R-form) were dissolved in 3 ml of methanesulfonic acid and 0.3 ml of anisole, and the solution was allowed to stand for 3 hours at 20° C. The mixture was then stirred into 20 ml of ether. The precipitating oily product was digested several times with ether, dissolved in a little water and purified by column chromatography.

($SiO_2$, Chloroform/methanol/conc. ammonia=20:20:5).

The obtained product was dissolved in the calculated amount of N/100-hydrochloric acid and evaporated in a high vacuum at 0° C.

The product was washed with ether and dried.
Yield: 50 mgm (25% of theory)
M.p.: 187°–190° C.

EXAMPLE 6

4-R-Spectinomycylamine trihydrochloride 2 gm of 6,8-bis-4-methoxybenzyloxycarbonyl-spectinomycylamine were dissolved in 10 ml of dioxane, and 10 ml of 4 N-hydrogen chloride in dioxane were added to the solution at 0° C. After stirring for 45 minutes the solution was filtered, and the residue was washed with ether.

Yield: 1.2 gm of a colorless powder
M.p.: 186°–188° C. (decomp.)
Mass spectrum of the silylated compound.
$M^+ = 765/693/621 = 333 + (4-6) \times 72$.

As indicated above, 4-spectinomycylamine, its R- and S- isomers, and non-toxic, pharmacologically acceptable acid addition salts thereof have useful pharmacodynamic properties. More particularly, they exhibit very effective antimicrobial activities in vitro as well as in warm-blooded animals, such as mice. Consequently, the compounds of the present invention are useful as broad-spectrum antibiotics.

4-R-Spectinomycylamine of the formula I was tested in comparison with the known antibiotic spectinomycin with regard to its effectiveness against *Staphylococcus aureus* SG 511, *Streptococcus aronson*, *Escherichia coli* ATCC 9637, *Pseudomonas aeruginosa*, *Serratia marcescens* ATCC 13 880, *Klebsiella pneumoniae* ATCC 10 031, *Proteus mirabilis* and *Proteus vulgaris*, and with regard to acute toxicity.

For these tests the method of the series-dilution essay in the microtiter system was used. The substances were tested in a fluid medium with regard to bacteriostasis. The effectiveness of the bacteriostasis was tested at the following concentrations: 80, 40, 20, 10, 5, 2.5, 1.25, 0.6 and 0.3 μgm/ml. A bouillon consisting of 5 gm of peptone, 3 gm of meat extract, filled up to a volume of 1000 ml with distilled water served as nutrient; pH-value 6.7.

The age of the primary cultures was 24 hours. The adjustment of the microorganism suspension was carried out with a photometer (according to Eppendorf) (diameter of the test tube 14 mm, filter 546 nm) by comparison with the turbidity of a barium sulfate comparison suspension produced by a suspension of barium sulfate which was prepared by addition of 3.0 ml of 1% barium chloride solution on 97 ml of 1% sulfuric acid. After the adjustment *streptococcus aronson* was diluted 1:150 and the remaining test microorganisms were further diluted with sodium chloride solution in the proportion of 1:1500.

16 mgm of the test substance was weighed in 10 ml measuring flasks and filled up with the solvent until the mark was reached. The further dilution series was prepared with distilled water or with the respective solvent.

0.2 ml of nutrient medium, 0.01 ml of the corresponding test substance dilution and 1 drop of the microorganism suspension were placed into the cavities of the microtiter plates and incubated for 18 to 20 hours at 37° C. A solvent control batch was always treated in like manner at the same time.

The reading was effected macroscopically, whereby the respective threshold concentration (=lowest still bacteriostatically effective concentration) was determined.

The following table shows the determined minimum inhibiting concentrations for the test substances:

| Microorganism | Minimum inhibiting concentration in μgm/ml | |
|---|---|---|
| | 4-R-Spectinomycylamine | Spectinomycin |
| *Staphylococcus aureus* SG 511 | 5 (2.5) | 20 (10) |
| *Streptococcus aronson* | 5 | 10 |
| *Escherichia Coli* ATTC 9637 | 20 (10) | 40 (20) |
| *Pseudomonas aeruginosa* | 40 (20) | 160 (80) |
| *Serratia marcescens* ATTC 13 880 | 10 | 20 |
| *Klebsiella pneumoniae* ATCC 10 031 | 10 (5) | 20 (10) |
| *Proteus mirabilis* | 10 | 10 |
| *Proteus vulgaris* | 5 | 10 |

The values in parentheses are the concentrations at which growth-reduction, but not a complete suppression of growth was observed.

The acute toxicity was determined by peroral and subcutaneous administration of both substances in increasing doses to white laboratory mice. The $LD_{50}$ represents the dose after which 50% of the animals died within 8 days. Both test substances had an $LD_{50}$ of more than 5 gm/kg; no animals died when either test substance was administered in an amount of 5 gm/kg. After subcutaneous injection both test substances had an $LD_{50}$ of more than 1000 mgm/kg; therefore they are for pratical purposes completely nontoxic.

For pharmaceutical purposes the compounds of the present invention are administered to warm-blooded animals perorally, parenterally or rectally, preferably parenterally, as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 1.6 to 33.3 mgm/kg body weight, preferably 8.3 to 16.7 mgm/kg body weight. The daily dose rate is 3.3 to 10.0 mgm/kg, preferably 16.6 to 33.3 mgm/kg.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 7

Hypodermic Solution

A lyophilizable sterile aqueous solution of 1000 mgm of 4-R-spectinomycylamine trihydrochloride is filled into a 5 ml-ampule, the solution is freeze-dried, and the ampule is sealed under aseptic conditions. An isotonic solution consisting of 5 ml of distilled water and 200 mgm of common salt is filled into another ampule under aseptic conditions, and the filled ampule is sterilized and sealed. Prior to use, the contents of the "dry" ampule are dissolved with the contents of the "wet" ampule, and the solution is injected.

EXAMPLE 8

Hypodermic Solution

The solution is compounded from the following ingredients:

| | |
|---|---|
| 4-R-Spectinomycylamine trihydrochloride | 1000.0 parts |
| Sodium chloride | 200.0 parts |
| Distilled water q.s.ad | 5000.0 parts by vol. |

Preparation:

The sodium chloride and the active ingredient are dissolved in the distilled water, the solution is filtered until free from suspended particles, and the filtrate is filled under aseptic conditions into 5 ml-ampules which are subsequently sterilized and sealed. Each ampule contains 1 gm of the active ingredient.

The free base, its R- or S-isomer, or any non-toxic, pharmacologically acceptable acid addition salt thereof may be substituted for the particular active ingredient in Examples 7 and 8. Likewise, the amount of active ingredients in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. The compound of the formula

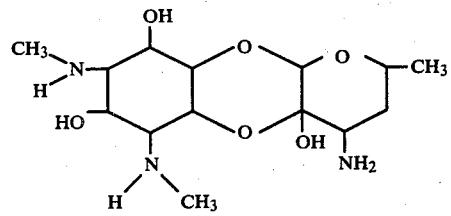

the R- or S- isomer thereof, or a non-toxic, pharmacologically acceptable acid addition salt of said compound or said isomer.

2. A compound of claim 1, which is 4-R-spectinomycylamine or a non-toxic, pharmacologically acceptable acid addition salt thereof.

3. An antibiotic pharmaceutical dosage unit composition consisting essentially of an inert pharmaceutical carrier and an effective antimicrobial amount of a compound of claim 1.

4. The method of destroying harmful microorganisms or suppressing their multiplication or growth in a warm-blooded animal, which comprises perorally, parenterally or rectally administering to said animal an effective antimicrobial amount of a compound of claim 1.

* * * * *

UNITED STATES PATENT AND TRADEMARK OFFICE
CERTIFICATE OF CORRECTION

PATENT NO. : 4,173,647

DATED : November 6, 1979

INVENTOR(S) : Roland Maier et al.

It is certified that error appears in the above-identified patent and that said Letters Patent are hereby corrected as shown below:

Column 5, line 24: "(s-" should be cancelled.

line 25: "inglet" should read -- (singlet --.

line 65: "solution was solution was" should read -- The solution was --.

Column 6, line 10: "trichloroethox-" should read -- trichloroethoxy --.

line 11: "ycarbonyl" should read -- carbonyl --.

line 16: "11.1" should read -- 11:1 --.

line 24: "methox-" should read -- methoxy- --.

line 25: "ybenzene" should read -- benzene --.

line 67: "sodum" should read -- sodium --.

UNITED STATES PATENT AND TRADEMARK OFFICE
CERTIFICATE OF CORRECTION

PATENT NO. : 4,173,647
DATED : November 6, 1979
INVENTOR(S) : Roland Maier et al.

It is certified that error appears in the above—identified patent and that said Letters Patent are hereby corrected as shown below:

Column 8, line 62: "trichloroe-" should read -- trichloro --.

line 63: "thoxycarbonyl" should read -- ethoxycarbonyl --.

Signed and Sealed this

Eighteenth Day of March 1980

[SEAL]

Attest:

SIDNEY A. DIAMOND

Attesting Officer     Commissioner of Patents and Trademarks